US008333508B2

(12) United States Patent
Reiner

(10) Patent No.: US 8,333,508 B2
(45) Date of Patent: Dec. 18, 2012

(54) MULTI-FUNCTIONAL MEDICAL IMAGING QUALITY ASSURANCE SENSOR

(76) Inventor: Bruce Reiner, Berlin, MD (US)

( * ) Notice: Subject to any disclaimer, the term of this patent is extended or adjusted under 35 U.S.C. 154(b) by 838 days.

(21) Appl. No.: 12/453,268

(22) Filed: May 5, 2009

(65) Prior Publication Data

US 2009/0279672 A1 Nov. 12, 2009

Related U.S. Application Data

(60) Provisional application No. 61/071,571, filed on May 6, 2008.

(51) Int. Cl.
*G01D 18/00* (2006.01)
*G06K 9/00* (2006.01)
(52) U.S. Cl. .......................... 378/207; 382/132
(58) Field of Classification Search ............... 250/252.1; 378/207; 382/132; 702/84
See application file for complete search history.

(56) References Cited

U.S. PATENT DOCUMENTS 5,905,262 A * 5/1999 Spanswick .................... 250/368
2007/0239377 A1 * 10/2007 Reiner ............................ 702/84

OTHER PUBLICATIONS

Gray et al., Joel E., "Radiation Physics: Test Pattern for Video Displays and Hard-Copy Cameras," Radiology, vol. 154, No. 2, Feb. 1985, pp. 519-527.

* cited by examiner

*Primary Examiner* — Vu Le
*Assistant Examiner* — Amara Abdi
(74) *Attorney, Agent, or Firm* — Jean C. Edwards, Esq.; Edwards Neils PLLC

(57) ABSTRACT

The present invention relates to a method of providing a quality assurance program for a medical imaging examination, including measuring quality assurance metrics, including at least one of motion, contrast resolution, spatial resolution, radiation does, noise, and anatomic positioning, using a quality assurance sensor; performing an analysis the quality assurance metrics data, comparing the data with norms for same; and providing quality assurance recommendations in real-time for adjustment of the quality assurance metrics during the examination. The sensor includes a sensor body having an upper surface and a flat lower surface, the flat lower surface being divided into more than one portioned segment; a plurality of sensors and test patterns embedded into said flat surface within each portioned segment; wherein the sensors and test patterns in each portioned segment take predetermined quality assurance metrics, to optimize image acquisition during the examination.

27 Claims, 6 Drawing Sheets

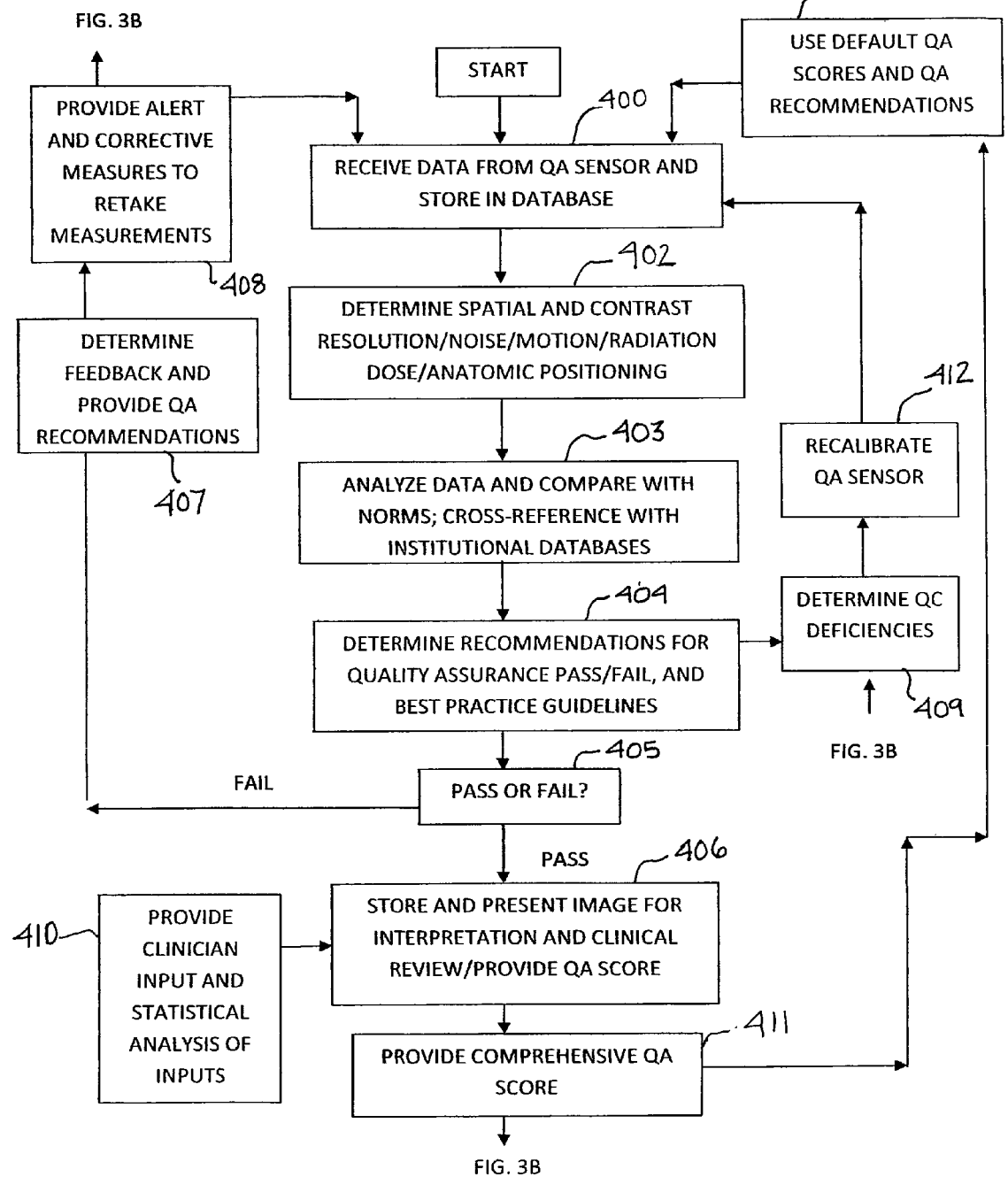

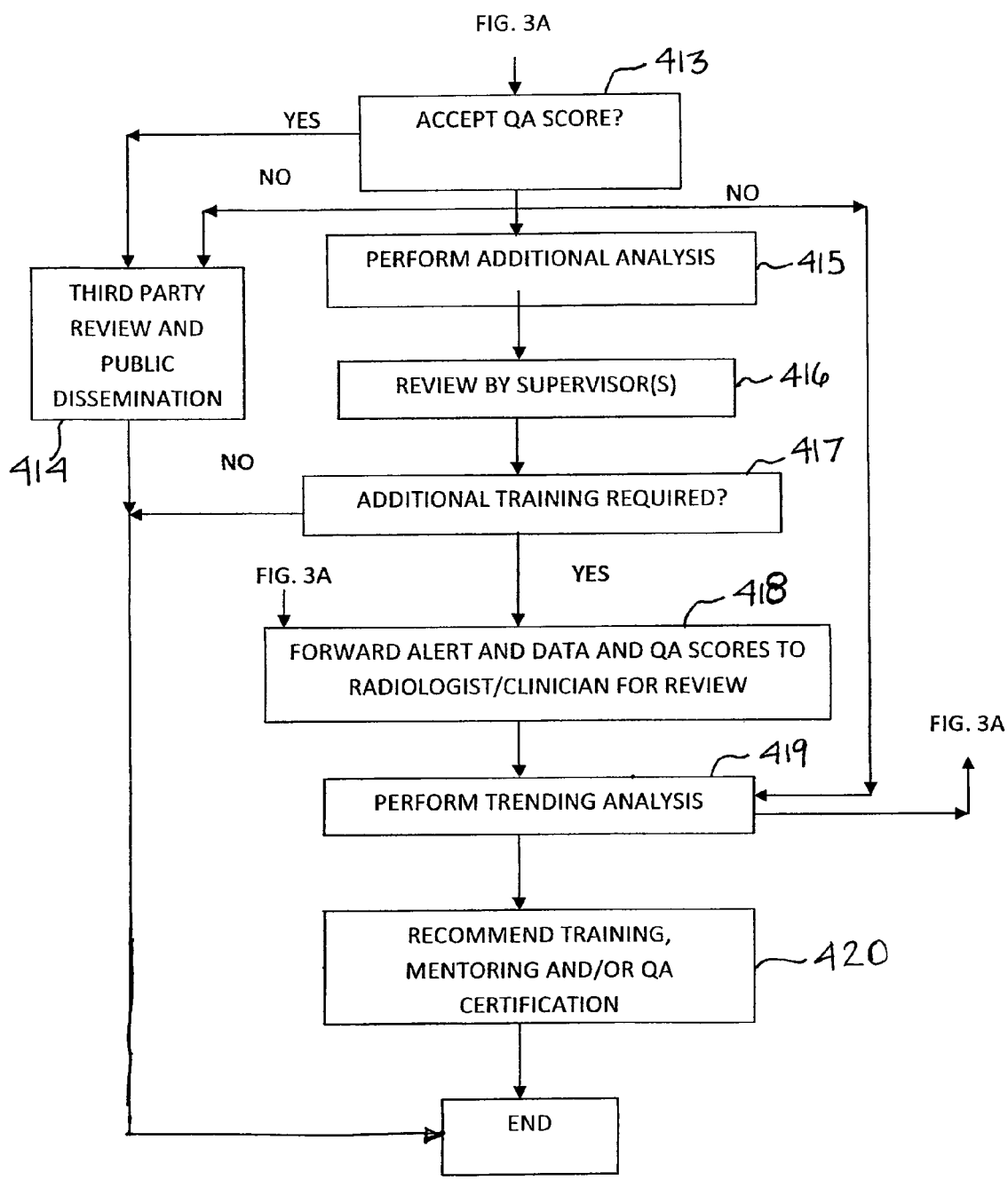

MULTI-FUNCTIONAL MEDICAL IMAGING QUALITY ASSURANCE SENSOR

CROSS-REFERENCE TO RELATED APPLICATIONS

The present invention claims priority from U.S. Provisional Patent Application No. 61/071,571, dated May 6, 2008, the contents of which are herein incorporated by reference in their entirety.

BACKGROUND OF THE INVENTION

1. Field of the Invention

The present invention relates to a quality assurance (QA) program in medical imaging that uses a sensor to obtain information from a patient, the information being used to track and analyze individual and collective QA performance and patient safety measures. Thus, the present invention combines QA and quality control (QC) technology to automate and objectify QA analysis, so that all medical imaging exams (and the patients in which these exams are performed) are analyzed in an identical and reproducible manner, regardless of the specific technology and personnel acquiring the imaging data.

2. Description of the Related Art

In current medical imaging practice, accountability and verifiability of quality standards can be divided into two separate and distinct exercises. The first exercise is quality control (QC), which is largely the domain of the medical physicist and equipment manufacturer. This consists of a series of periodic surveillance tests aimed at ensuring that the physical performance capabilities of the equipment used for medical imaging acquisition (e.g., computerized tomography (CT) scanner) is in keeping with pre-defined quality standards. In this endeavor, the acquisition device is externally tested using a series of phantoms to ensure that a number of quality-centric metrics are maintained in accordance with industry-wide standards. This form of quality testing is performed independent of the patient and the specific clinical scenario in which the medical imaging application is being utilized. Simply stated, it is a "one size fits all approach" to quality assessment, in which the data is largely viewed in a vacuum.

The second form of quality assessment within medical imaging is quality assurance (QA), which is clinical in its orientation (as opposed to the technical orientation of QC). Whereas QC is the domain of the medical physicist and equipment manufacturer (i.e., technical practitioners), QA is primarily the domain of the clinical practitioners, which include the imaging technologist, radiologist, and clinician. In the practice of QA, these clinical practitioners are tasked with the assessment of image quality, and the corresponding ability to discriminate between "normal" and "pathologic" states within the medical imaging dataset. While the performance of all three stakeholders are largely affected by image quality, the principal party tasked with QA assessment in current medical practice is the imaging technologist, who performs QA assessment at the point of image acquisition (i.e., image capture), and determines whether the imaging dataset obtained is of sufficient quality (i.e., pass or fail), and can be subsequently submitted for radiologist and clinician interpretation. Unlike the case with QC, which is external to the patient and performed on a periodic basis, QA is intrinsically tied to the clinical circumstances prompting the imaging examination. As a result, the QA assessment process must be performed in the relative context of each individual patient (e.g., body habitus, mobility) and clinical indication (e.g., specific reason for testing, overall morbidity).

To a large extent, this clinical assessment of medical imaging quality (QA) is largely subjective in nature, due to the lack of reproducible objective imaging quality metrics. The one exception is mammography, which has well defined imaging quality standards as defined by the Mammography Quality Standards Act (MQSA). QA standards for the remaining medical imaging modalities are largely left to the individual discretion of the imaging provider, with the technologist performing the image acquisition playing the principle role of QA protagonist. In reality, this current QA model is inherently flawed, for it relies on the subjective evaluation of individuals who have variable degrees of clinical experience, QA education and training, and oversight.

The large inter-technologist and inter-institutional QA variability is further compounded by the fact that the subjective methodology used for QA assessment is not recorded, tracked, or analyzed on a consistent and reliable basis. Thus, a method and apparatus, which is objective but user-specific, to automate the collection, storage, and analysis of QA metrics, and perform a QA assessment during medical imaging, on a consistent and reliable basis, is desired.

SUMMARY OF THE INVENTION

The optimum quality program in medical imaging would include the creation of a combined QA/QC technology that would automate and objectify QA analysis, so that all medical imaging exams (and the patients in which these exams are performed) are analyzed in an identical and reproducible manner, regardless of the specific technology and personnel acquiring the imaging data. A number of objective quality-oriented medical imaging metrics would be established using data provided from a QA sensor, to quantify the QA process, and these metrics would then be automatically recorded into a QA database, which could be used to track and analyze individual and collective QA performance and patient safety measures. With the creation of an automated QA database (and defined QA standards), "best practice" guidelines could be established based on meta-analysis of the QA databases.

In one embodiment consistent with the present invention, data is acquired at the level of the QA sensor (acquisition device), and the data is synchronously populated into multiple QA databases (including information on modality, patient, technologist, technology, exam, and clinical), with data storage being held at the level of multiple information system technologies (i.e., modality, Radiology Information System (RIS), Picture Archiving and Communication System (PACS), Electronic Medical Report (EMR)).

In another embodiment consistent with the present invention, associated data is acquired (i.e., radiation profile, just noticeable difference (JND) metric, patient profile) and is cross-referenced with the calculated QA data from the QA sensor.

In another embodiment consistent with the present invention, automated decision support feedback is provided to the operator (e.g., technologist, radiologist, clinician, administrator, physicist) at the point of contact. The decision support features are task and operator dependent (i.e., optimized exposure parameters for technologist, optimized image processing parameters for data review and clinical assessment by radiologist/clinician, radiation dose versus quality measures for physicist/administrator, comparative technology image quality scores for vendor).

In another embodiment consistent with the present invention, longitudinal task and operator-specific QA analysis is also provided (downstream) through prospective meta-analysis of QA data (i.e., correlative scores of image quality and diagnostic accuracy for radiologist, cumulative image quality/radiation scores for technologist and medical physicist, comparative institutional image quality scores (administrator), comparative technology image quality scores (vendor), cumulative image quality and clinical outcomes analysis (clinician).

In another embodiment consistent with the present invention, QA analytical data from QA meta-analysis is routinely presented to each stakeholder for review, with comparative peer-review QA data. These comparative scores are associated with educational/training data to facilitate quality improvement.

In another embodiment consistent with the present invention, trending analysis also performed to identify differential QA metrics over time, along with impact of QA intervention (i.e., educational/training programs, QA certification, and QA consultation).

In another embodiment consistent with the present invention, QA data is analyzed by a designated third party non-profit, to document veracity and authenticity of data, and is made available for public dissemination (Internet, publications).

In another embodiment consistent with the present invention, QA data outliers (i.e., excessive radiation, manually overridden (technologist accepted, multiple exam repeats), are automatically recorded in a QA deficiency database, which triggers a mandatory QA data review by a multi-disciplinary QA team (technologist, radiologist, administrator, physicist, vendor). Repeated violations and/or unexplained QA errors are grounds for suspension of clinical privileges, FDA approval, and/or mandatory QA educational programs.

In another embodiment consistent with the present invention, the derived QA data can be verified and validated through an external review process, monitored by a symposium of QA experts within industry and medical practice to ensure all QA data is reproducible and consistent with industry-wide standards.

In another embodiment consistent with the present invention, the QA data recorded and subsequently analyzed through meta-analysis of multi-institutional databases can in turn be used to create new QA-centric technologies, (i.e., acquisition and QA data from patients with excessive noise and motion measurements can be used to test and create new software program (image processing) for selective use in non-compliant or morbidly obese patients).

In another embodiment consistent with the present invention, meta-analysis of QA and clinical outcomes data can be used to create evidence-based medicine (i.e., best clinical practice) guidelines, which in turn can utilize the QA data to ensure compliance (i.e., EBM radiation dose standards for pediatric chest radiography in the diagnosis of pneumonia, can identify the optimum radiation dose/quality ratio, and once derived, can be used to assess that these "best clinical practice" standards are being routinely used by imaging providers).

In another embodiment consistent with the present invention, the QA sensor and derived QA data can be collectively used for governmental (e.g., FDA) regulatory efforts and approval processes. As an example, a new technology being submitted for FDA approval must pass the pre-defined QA requirements (as directly measured by QA sensor technology) and demonstrate appropriate clinical outcomes (through longitudinal QA/clinical data analysis).

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIGS. 3A and 3B are flow charts which show the operation of a QA program using the QA sensor, according to one embodiment consistent with the present invention.

DESCRIPTION OF THE INVENTION

Figure 1:
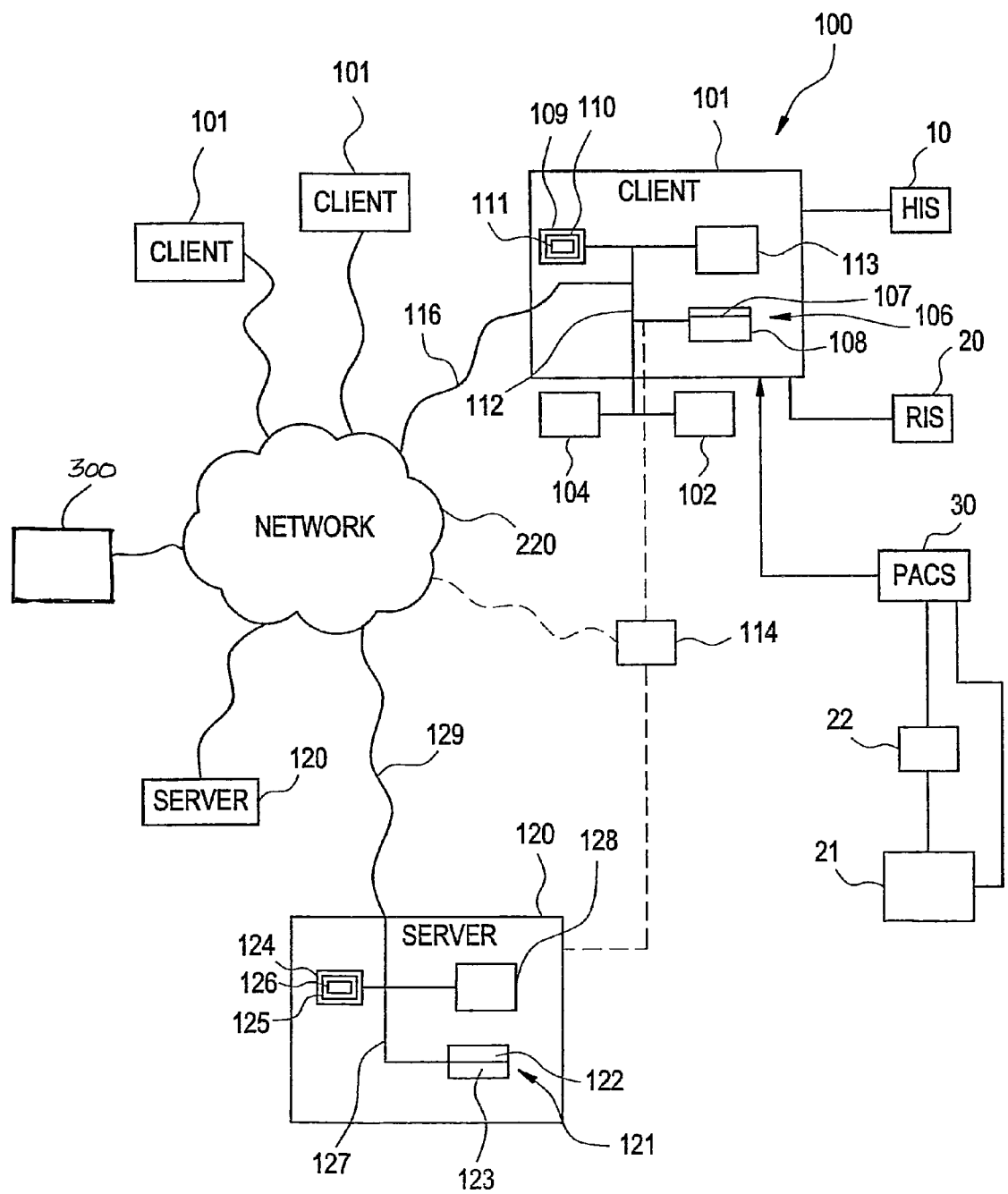
FIG. 1 is a schematic drawing of the major components of a radiological system using a QA sensor, according to one embodiment consistent with the present invention.

According to one embodiment of the invention, as illustrated in FIG. 1, medical (radiological) applications may be implemented using the system 100. The system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, a QA sensor 300, and/or other systems. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, radiographic device 21, CR/DR plate reader 22, PACS 30, and QA sensor 300, etc., may be enabled to allow the system 100 to retrieve and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely. According to another embodiment of the invention, the client computers 101 may include several components, including processors, RAM, a USB interface, a telephone interface, microphones, speakers, a computer mouse, a wide area network interface, local area network interfaces, hard disk drives, wireless communication interfaces, DVD/CD readers/burners, a keyboard, and/or other components. According to yet another embodiment of the invention, client computers 101 may include, or be modified to include, software that may operate to provide data gathering and data exchange functionality.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the client computer system 101 may include an input or other selection device 104 which may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus 104. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS 30 and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the client computer 101 may include an image display device 102 which may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate), are shown as directly coupled to the client computer 101, it is known that these systems may be indirectly coupled to the client over a LAN, WAN, the Internet, and/or other network via communication links. Further, even though the QA sensor 300 is shown as being accessed via a LAN, WAN, or the Internet or other network via wireless communication links, it is known that the QA sensor 300 could be directly coupled using wires, to the PACS 30, RIS 20, radiographic device 21, or HIS 10, etc.

According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

The present invention relates to a QA sensor 300, which is a relatively small, multi-functional portable device, which performs the combined functions of, for example, an anatomic marker, a QA phantom, and a sensor for obtaining quantitative measurements. The QA metrics which are measured and analyzed using the device including (but not limited to) motion, contrast resolution, spatial resolution, radiation dose, noise, and anatomic positioning. In addition to obtaining direct and indirect measurements of these QA variables, the invention can also be used to record, characterize, and analyze anatomic positioning, examination type, and identifying data specific to the individual patient, technologist, and technology being employed. (This latter data can be automatically recorded by integrating the QA sensor with Bio-metrics (see pending U.S. patent application Ser. No. 11/790, 843, dated Apr. 27, 2007, which is herein incorporated by reference), at the level of the modality.

Figure 2A:
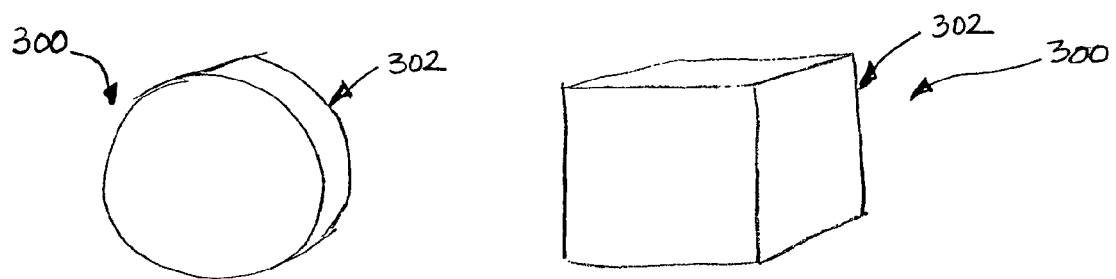
FIG. 2A is a perspective view of two possible designs of a QA sensor, according to one embodiment consistent with the present invention.
Figure 2B:
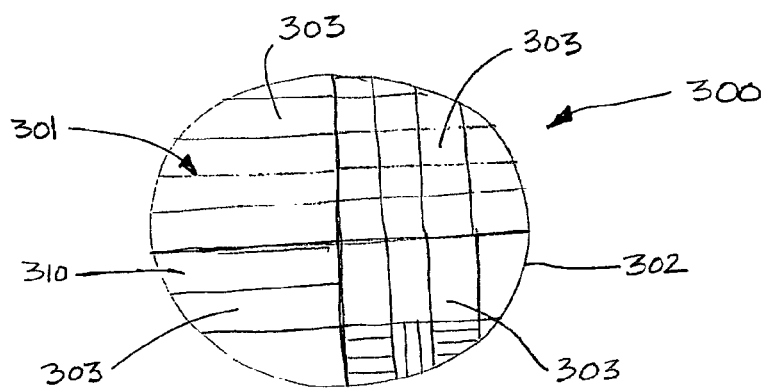
FIG. 2B is a bottom view of a QA sensor, with one representative example of a sensing grid thereon, according to one embodiment consistent with the present invention.
Figure 2C:
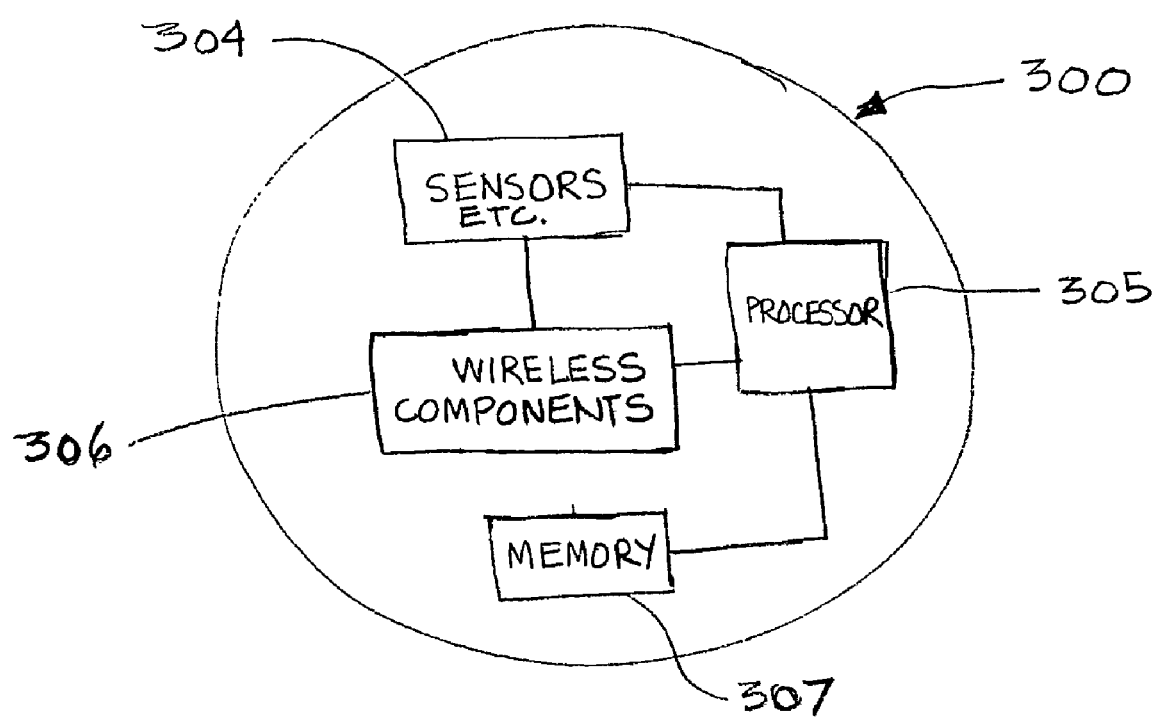
FIG. 2C is a schematic view of the internal components of a QA sensor, according to one embodiment consistent with the present invention.

In particular, the QA sensor 300, as shown in FIGS. 2A-2C, would include a relatively small device which can be placed on a subject's body, without obscuring their anatomy. The sensor 300 can be in a round or cubed shape (see FIG. 2A), and one of ordinary skill in the art would know that as long as the sensor 300 includes the features desired, it can be of any shape. The sensor 300, as shown in FIG. 2B, would have a series of sensors and test patterns 301 which are embedded into the flat surface 302 of the bottom surface of the sensor 300. The sensor series and test patterns 301 would be divided into multiple portioned segments 303 (i.e., four individual quadrants), according to the desired pattern. The sensor 300 may include, for example, an adhesive strip or other holding mechanism, which would keep the sensor in place on the body. Thus, in operation, the user would position the sensor 300 directly onto a patient's skin surface preceding image acquisition. The present invention can also take the form of a single sensor 300, in addition to the use of multiple sensors 300.

According to one embodiment of the invention, and as shown in FIG. 2C, the QA sensor 300 may include several modules, such as sensors 304, a processor 305 to analyze the information, and wireless technology 306 to send the data to the PACS 30 or other equipment. Further, a memory 307 could be included for data storage within the sensor 300 for later download. The modular construction facilitates adding, deleting, updating and/or amending modules therein and/or features within modules. One skilled in the art will readily appreciate that the invention may be implemented using individual modules, a single module that incorporates the features of two or more separately described modules, individual software programs, and/or a single software program.

The components and individual measurements contained within the QA Sensor 300 would vary depending upon the individual imaging modality being used, with a different QA sensor 300 with a different group of sensor series and test patterns 301 being required for each of these modalities. The following discusses the components that would be included in a QA sensor 300 directed to radiography, mammography, computed tomography (CT), nuclear medicine, and magnetic resonance imaging (MRI). All the information taken by the sensor 300 is provided to the client computer 101, whether by wireless technology or by directly over wire. The information is analyzed by the program 110, can be displayed to the user on the display 102, and stored in the database 113, as described above.

A. Radiography and Mammography

The sensor series and test patterns 301 may include, for example, a series (or grid) of lines and grey scales designed to provide objective measurement of contrast and spatial resolution, for example, to test and optimize the image acquisition. Specifically, a series (or grid) of lines and grey scale patterns can be incorporated into the QA sensor 300, which information can then be used by the program 110 to objectively quantify spatial and contrast resolution through both visual and computational analysis. Spatial resolution is defined as the ability to discriminate between two adjacent objects (e.g., lines), while contrast resolution is defined by the ability to resolve small differences in density, quantifying the dynamic range of contrast within the designated area of the sensor grid 301 which contains different levels of contrast, including higher electron density (e.g., similar to bone), intermediate electron density (simulating soft tissue), and low electron density (simulating air).

An additional designated area 303 of uniform density within the sensor grid 301 can be used to quantify noise, by measuring the variability in individual pixel values contained within the region of interest. By the program 110 calculating multiple pixel values within this region of interest (of uniform density), noise can be derived by determining the variability in pixel values (i.e., field inhomogeneity).

Motion can be derived by placing a series of sharply defined patterns (e.g., cross) at different depths within the grid and having the program 110 deriving the degree of motion in the x, y, and z-axes based on deviations in the actual image from the expected image.

Radiation dose can be directly quantified by placing a radiation sensor (e.g., miniature thermo-luminescence dosimeter) within the grid 301 and having the program 110 correlating the "actual" radiation dose at the skin level, with the delivered radiation dose (obtained from acquisition exposure parameters). This serves the dual role of creating a mechanism for radiation parameter/dose calibration.

An additional feature of the radiation sensor (and radiation dose measurements) is the ability to determine the inflection point at which maximal radiation dose reduction can be obtained without crossing a pre-defined threshold in image quality (see pending U.S. patent application Ser. No. 11/976,518, dated Oct. 25, 2007, which is herein incorporated by reference in its entirety). Using an objective measure of image quality (e.g., just noticeable difference (JND) metric), a test exposure using ultra-low dose radiation can be performed and the optimal exposure parameters for maximal dose reduction can be derived by the program 110, after correlating the JND-metric output with the derived QA measurements for spatial resolution, noise, and motion (which are dose dependent). The present invention can thus be utilized in a feedback loop in which a very small test dose is obtained, the quality and dose measurements can be made using the present invention, and based on those parameters, optimal acquisition settings can be made for a subsequent clinical exposure/patient study.

Anatomic positioning can be derived by the program 110 from placement of multiple sensors 300 in the anatomic region being imaged. If as an example, a frontal chest radiograph is being performed, sensors 300 may be positioned at the four corners of the anatomic periphery. If any of the sensors 300 do not achieve equal measures of exposure, then there is some degree of malpositioning (i.e., anatomy cut-off), which provides direct feedback to the operator as to the magnitude and location of diminished radiation activity.

The ability to create QA sensors 300 using miniaturization provides a way to make the sensors extremely small in size so that they do not obscure visualization of the anatomy being evaluated. In addition to placing sensors 300 over the anterior (i.e., frontal) skin surface, sensors 300 can also be placed over the posterior (i.e., back) skin surface, thereby providing a mechanism to indirectly measure the amount of radiation absorbed by measuring the exposure at both skin surfaces. These data are particularly important in quantifying image and exam-specific QA, because it provides a mechanism to account for variability in patient body habitus.

For example, an obese patient would have a far greater degree of absorbed photons then a comparable patient of thin body habitus. By combining the data of multiple QA sensors 300 positioned over different anatomic regions, comparative QA data can be used by the program 110 to measure and subsequently optimize exposure parameters and radiation dose, especially if the test dose methodology is used.

The QA data derived from the QA sensors 300 can in turn provide objective, real-time feedback to the technologist or operator at the point of image capture. The data can be analyzed by the program 110 in a number of different ways; the most simple of which can consist of a pass/fail recommendation based upon pre-defined image quality metrics. Alternatively, the program 110 can provide the technologist or operator with a detailed analysis of individual QA metrics, along with computer-derived recommendations for quality improvement. As an example, if excessive motion was detected by the sensor 300, the program 110 may recommend adjustment in the acquisition parameters in order to reduce the exposure time (and resulting motion).

The program's 110 analysis of the QA data obtained by the sensor 300 may be used to optimize post-acquisition image processing. If, for example, the contrast resolution was found to be minimally deficient based on an analysis of the information obtained by the sensor 300, the program 110 may recommend the application of certain image processing parameters to enhance those areas within the image (e.g., soft tissues) which were found to have diminished contrast resolution on the initial QA analysis.

By creating a mechanism to directly capture standardized QA data intrinsic to each exam, patient, and technology being used, QA databases 113 (proprietary or non-proprietary) can be created as a direct output of the QA sensors 300. These QA databases 113 can be cross-referenced by the program 110 with other institutional QA databases to perform QA meta-analysis, which in turn can be used to establish data-driven best practice guidelines (which is the core construct of evidence-based medicine).

B. Computed Tomography (CT)

Some differences exist between radiography/mammography and CT, which affect QA sensor technology. While conventional radiography and mammography are two-dimensional imaging acquisitions, CT obtains data in three dimensions (i.e., volumetrically), and as a result, requires a three-dimensional QA sensor 300.

An additional difference is the number of individual images contained within a single medical imaging examination. The typical radiographic examination consists of 1-4 images, while the typical multi-detector CT exam consists of 300-800 or more images. As a result, the distribution of the QA sensors 300 on the anatomy should reflect these differences, in order to record QA data in multiple images. While this can be accomplished in several ways, the simplest would be to position QA sensors 300 at the periphery of the anatomy being imaged, along with several intervening data points. The collection of multiple QA data points provides a mechanism to adjust exposure parameters in keeping with changes in anatomy. As an example, as one moves from the air-containing inferior thorax to the upper abdomen, dramatic changes in tissue composition and density occur, resulting in marked differences in tissue absorption and radiation dose requirements for the CT study. QA sensors 300 positioned over the lung base and liver may be only 5 cm apart from one another, yet yield different QA measurements. The differential QA data derived from these QA sensors 300 can be used by the program 110 to intelligently adjust CT exposure parameters as different anatomic regions are being imaged.

The differential QA data also provides a reliable mechanism to provide anatomy-specific QA data, which can guide repeat imaging, in the event of a "failing" QA grade by the program 110. If for example, the QA sensors 300 were positioned at 5 cm intervals over the anatomic region being imaged, a deficient QA score in sensor #6, for example, could identify the specific anatomic region requiring re-imaging. If the adjacent QA data from sensor #7 demonstrated a "passing" QA grade by the program 100, then selective repeat imaging could be performed and the "final" imaging dataset which is archived and presented for interpretation and clinical review by the program 110, would selectively incorporate the highest QA scores, resulting in a continuous imaging dataset composed of the highest QA imaging data subsets. The adjustments can be made in "real time" during the scan depending on whether the estimation of absorbed dose based on the CT scannogram proves to be accurate based on the direct measurements from the sensors 300 associated with the present invention.

C. Nuclear Medicine

While the QA sensor 300 technology used for radiography, mammography, and CT would be similar to one another in many respects, the QA sensor technology for nuclear medicine would be far different. This is primarily due to the fact that nuclear medicine studies utilize radioisotopes as their source of radiation. As a result, the QA sensor 308 for nuclear medicine would include a "cold" phantom, which is distinct and separate from the "hot" background caused by the radioactive isotope absorbed within the anatomic region of interest.

Figure 2D:
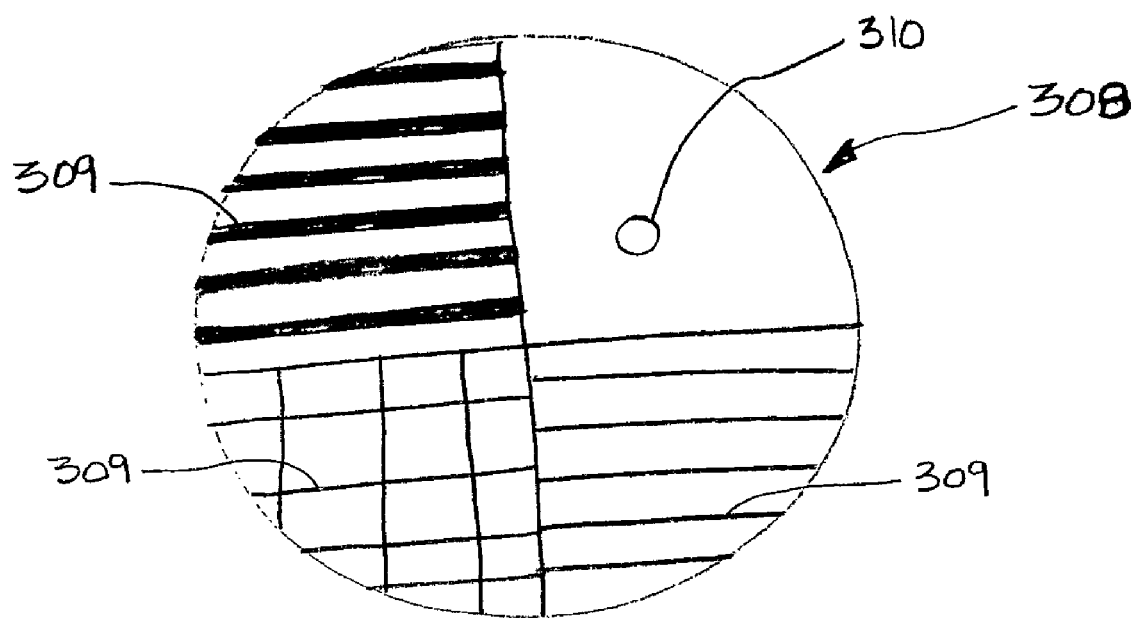
FIG. 2D is a bottom view of a QA sensor according to another embodiment consistent with the present invention.

The components of the QA sensor 308 (see FIG. 2D) for nuclear medicine would be similar in nature to the QA sensor 300 previously described. Defined line patterns 309 embedded in the "cold" QA sensor 308 would provide for calculation of spatial resolution, while patterns of differential thickness provide a mechanism to calculate contrast resolution. The thicker areas would demonstrate higher absorption of the radioactivity, in comparison to the thinner patterns embedded in the sensor 308, thereby creating differential radiation-induced contrast, which can be quantified.

Quantification of motion can be derived from placing a small hole 310 within the QA sensor 308, or by the sharpness of visualization of the line patterns 309. Any inherent motion within the nuclear medicine dataset will be detected and quantified by the program 110, by measuring the outline and degree of fuzziness relative to the borders of this hole 310 or the pattern of these lines 309. Noise could be indirectly calculated by the program 110 in a manner similar to the radiography QA sensor 300 by measuring variability in pixel radiodensity within a defined region of interest.

An external radiation sensor is not required for radiation dose calculation within nuclear medicine since all radiation is internal to the patient.

Because of inherently decreased resolution with nuclear medicine imaging, (compared with CT), the required size of the nuclear medicine sensor 308 would be larger than the CT QA sensor 300. As a result of this size differential, the number of nuclear medicine QA sensors 310 which can be utilized (without obstructing critical anatomy), may be less than allowable for CT.

D. MRI

Because MRI does not have associated ionizing radiation, no radiation sensor is required. One method to measure contrast resolution for MRI includes creating four (4) small compartments 303 within the MRI QA sensor 300, each containing material of different signal characteristics 304, which would contain chemical substances comparable to anatomic structures (e.g., water, air, soft tissue, fat). Contrast resolution could be derived by the program 110 calculating the MRI signal ratios between the multiple (e.g., 4) different solutions 304 contained within the QA sensor 300, and comparing with the known signal ratios of the substances.

Spatial resolution could be derived by the program 110, by the placement of a hypointense (i.e., devoid of MRI signal) line grid 311 (see FIG. 2B) within a high signal intensity solution, which creates lines 301 (from the hypointense grid) against the background of the high signal intensity fluid.

Noise would be calculated by the program 110 in a similar manner to CT, by measuring the degree of signal inhomogeneity within each of the four compartments 303, which each consist of a uniform signal intensity fluid.

Motion can be determined by measuring the border sharpness of a character contained within the QA sensor 300.

In operation, upon image acquisition, the QA measurement tools incorporated into the QA sensor device 300, 308 record individual data for each QA metric, and transfers these measurements via wireless technology to a computer 101, where the program 110 stores the data in a series of structured QA databases 113 simultaneously residing in the imaging modality (e.g., CT scan), radiology information system (RIS) 20, picture archival and communication system (PACS) 30, and electronic medical record (EMR). The directly acquired QA data measurements obtained by the QA sensor 300, 308 are then analyzed by the program 110 by comparing the measured values against established QA norms, which are statistically defined as within normal limits, based upon a number of variables contained within the QA database 113. These variables can include (but are not limited to) the anatomic region being imaged (e.g., breast), the modality utilized (e.g., mammography), patient physical characteristics (e.g., breast size and tissue composition) and clinical indication (e.g., re-evaluate mass). By the program 110 prospectively cross-referencing the QA sensor 300, 308 data measurements with those of similar profiles within the QA databases 113, individual QA outliers (as well as a comprehensive QA score) can be identified at the point of image capture and presented by the program 110 to the technologist or radiologist for review.

While the methodology for data presentation can vary, one simple manner in which the data can be presented by the program 110 might include a color coded readout, which identifies all passing QA scores in green (i.e., values within one (1) standard deviation (SD) of the mean, borderline QA scores in yellow (i.e., greater than 1 SD of the mean, but less than 2 SD), and failing QA scores (i.e., greater than 2 SD of the mean) in red. These individual QA scores can also be incorporated by the program 110 into a comprehensive QA score, which selectively weights the individual QA metrics based on criticality to overall image quality, and creates a mathematical score tied to overall image quality.

Once these individual and collective image quality scores are presented to the technologist, he/she has the option to act in accordance with the program 110 derived QA analysis (i.e., accept "as is"), request additional analysis (i.e. additional QA data query), or over-ride the program 110 derived QA analysis (i.e. reject).

The technologist-generated actions are also recorded in the QA database 113, for the purposes of education and training. If, for example, a technologist is observed to repeatedly reject the program 110 recommendation to repeat an image due to measured QA deficiencies, this data can be analyzed by a supervisory technologist, radiologist, or administrator. Based upon this QA review process, additional technologist training may be recommended (can also by automatically performed by the program 110), in accordance with the specific QA deficiency in error.

On the other hand, a technologist may be rejecting QA images deemed "passable" by the program 110 derived QA analysis, which is found on further review to represent data error. In this situation, the corresponding technology in error (e.g., data from the QA sensor 300, 308) may require recalibration of the sensor 300, 308 in order to improve performance. In this manner, the QA review (of both the client computer 101, sensor 300, 308, and technologist) is an iterative process, which is continuously being updated and refined, with the goal of improving QA performance based upon feedback and education/learning.

An additional feedback component of the present invention, is clinical input provided by the radiologist and/or clinician, which can be performed at the level of the PACS 30 and/or EMR when the images are reviewed for interpretation and/or clinical review. The program 110 can request that the radiologist or clinician provide subjective QA input for each imaging exam reviewed. This may include an automated pop-up menu on the display 102 at the time of exam closure, which requests an overall image quality score (e.g., on a scale of 1 to 5), along with identification of specific QA deficiencies in the event of poor image quality. These subjective QA scores are incorporated into the QA database 113 by the program 110, and are also used in the analytical process, with attribution of the individual radiologist/clinician providing input. Statistical analysis of this subjective QA input provides a mechanism to weight subjective scores in accordance to the end-user QA profile. For instance, since one radiologist may consistently provide low QA scores, while another radiologist consistently provides high QA scores (in excess of his/her peers), the QA analysis derived by the program 110 from the database 113 can take into account these radiologist-specific differences by applying a weighting factor to the QA analysis.

Further, when the radiologist/clinician selects QA deficiencies which are contradicted by the program 110 and additional peer references, an educational alert is activated by the program 110, providing the radiologist/clinician with the discrepant data and corresponding images. If desired, the radiologist/clinician can query the QA database 113 for corresponding images to assist with QA deficiency classification. If, for example, the radiologist is mistakenly mischaracterizing "noise", the program 110 can check the QA database 113 to identify a series of images with different QA scores for noise and present these images and matched scores to the radiologist for review. In this manner, the QA database 113 (and data derived from the QA sensor 300, 308) serves an important educational/training role.

Once a single or multiple QA deficiencies are identified by the program 110 based upon the QA sensor data and a check of the corresponding QA database 113, an automated prompt is sent by the program 110 to the technologist performing the exam (at the imaging modality), to alert them to the particular type and magnitude of the QA deficiency and to advise reacquiring the image(s) after correction of the identified QA deficiency. Specific QA interventions (i.e., corrective measures) will be presented to the performing technologist by the program 110, based on the specific QA deficiency identified and comparative analysis of the QA database.

An example of how this specific function works is provided as follows. In the performance of a digital chest radiographic exam, a series of QA metrics are automatically measured by the program 110. Among the various QA variables analyzed, excessive noise is identified by the program 110, causing the overall image quality to be adversely affected. In addition to providing instantaneous feedback to the technologist performing the exam (at the point of image capture), the program 110 queries the QA database 113 to determine 'acceptable" levels of noise for this exam type (digital chest radiograph) and this particular patient (John Doe), or similar patient profile (large body habitus, poor mobility, ex-smoker). The program 110 identifies that the quantitative noise level measured is 28% higher than the expected upper limits of normal in this particular patient and exam type, and provides the technologist with a recommended intervention (increase mAs from x to y).

In addition to the QA metrics described above, the QA sensor 300, 308 placed upon the skin surface of the patient can also record laterality (e.g., right, left), patient positioning (e.g., supine, erect), exam type (e.g., digital subtraction chest radiography), and specific identifying information of patient, technologist, and technology utilized.

In addition to quantifying specific QA metrics within the acquired image, the QA sensor 300, 308 can also be used to facilitate radiation dose reduction. This involves obtaining a scout or test image by using an ultra low radiation dose (e.g., 1/10 normal dose). By utilizing the QA data derived from the QA sensor 300, 308 for this test image, the program 110 can effectively calculate optimal exposure parameters for the "real" imaging dataset being performed. This feature would be analogous to the "red eye" feature on a camera, which utilizes sample visual data to optimize exposure parameters for the "final" photographic image being obtained. The ability of the program 110 to cross reference "technical" (e.g., exposure parameter) and "clinical" (e.g., clinical indication) data, provides a more in-depth analysis in determining the appropriate balance between maximal dose reduction, minimal image quality, and the clinical circumstances being evaluated.

Optimizing patient safety through radiation dose optimization is another important outcome of the QA sensor 300, 308. Direct calculation of radiation dose exposures is provided by the QA sensor 300, 308, and this data can be cross-referenced by the program 110 with additional radiation and exposure data points within the patient and exam-specific QA databases 113. If, for example, a technologist is performing an abdominal/pelvic CT exam on a patient who has had three similar exam types in the past, the program 110 will provide the technologist with reference data from the current and prior examinations, along with recommended acquisition parameters to achieve different levels of radiation dose reduction. By integrating quantitative image quality software programs 110 (e.g., JND-metric), scout images using different exposure parameters (and different radiation doses) can be acquired and comparatively analyzed to identify the optimum inflection point in balancing image quality and radiation dose optimization.

As an example, the same patient may be under a chest radiograph for two different clinical indications. In the first example, the exam is being performed to evaluate the possibility of a cancer, in which case the requirements for minimizing noise and maximizing resolution are high, thereby limiting the extent of allowable radiation dose reduction. In this second example, the clinical indication is line placement, which allows for more aggressive radiation dose reduction (and reduced image quality), since the principal clinical task consists of visualizing the line, as opposed to detecting an occult cancer. These analyses can be further adjusted by the program 110 searching the clinical/imaging databases 113 and determining that the line placement radiographic study is a follow-up exam to a similar radiographic study done earlier the same day. The temporal proximity provides even greater justification for aggressive dose reduction, since the anatomy and potential pathology were previously evaluated on the earlier same-day exam. These examples illustrate the fact that QA sensor data provides an important tool to synergistically optimize radiation dose reduction and image quality. The derived QA data can be analyzed by the program 113 in conjunction with imaging and clinical data (from the PACS 30 and EMR) to refine the analysis and improve the data output.

The data derived form the QA sensor 300, 308 and comparative analysis has the potential to provide automated decision support to the various stakeholders. For a technologist tasked with optimizing image quality during image acquisition, the QA database 113 can be mined by the program 110 prior to image acquisition (at the point of order entry), and default acquisition parameters presented to the technologist with recommended exposure parameters and protocol, based upon available QA data.

For example, a technologist scheduled to perform a portable chest radiograph on a patient in the intensive care unit can have default exposure parameters presented by the program 110 based upon the same patient's QA database 113, where the program 110 has sorted through prior imaging data and identified those acquisition parameters associated with the highest QA scores.

In another example, a technologist preparing to perform an abdominal/pelvic CT exam on an oncologic patient can have the QA database 113 automatically queried by the program 110 to identify those technical parameters associated with the highest image quality, based upon both the QA data from the QA sensor 300, 308, along with subjective quality data input from clinicians/radiologists. In this automated query, multiple QA databases 113 can be automatically mined by the program 110, including information on the specific patient to be examined, as well as other QA databases 113 from patients with similar clinical profiles. In this analysis, acquisition profiles are presented by the program 110 (based upon prior abdominal CT image quality scores), along with other technical parameters that contribute to CT image quality, including (but not limited to) collimation (i.e., CT slice thickness), the CT kernel employed, and the volume and rate of intravenous contrast administration.

The automated decision support provided by the program 110 to radiologists/clinicians for image review and analysis would focus on optimizing the image presentation state, in accordance with the individual preferences of each examiner (based upon a QA profile of individual preferences based upon his/her input of prior imaging data). This recommended QA data could include recommendations for post-acquisition image processing, application of specialized filters (e.g., for noise reduction) and 2-D or 3-D reconstructions.

The decision support features for administrators and medical physicists could focus on radiation safety and provide detailed information and recommendations by the program 110 regarding the optimized radiation dose/image quality ratio (as previously described), in accordance with the patient and clinical profiles. Technology vendors would also have support features (aimed at improving product development and refinement), by having comparative QA data presented by the program 110 based upon a specific technology's QA metrics relative to competing technologies. In addition, QA data can be utilized to enhance or refine products in development.

As an example, a CT vendor may be developing filters for noise reduction in ultra low dose CT. As new filters are created and tested, the program 110, using the corresponding QA database 113, can provide specific data regarding measured and perceived noise levels relative to different radiation dose levels, as well as the radiation/image quality ratios. Using this combined QA data, the vendor can test multiple versions of the software program 110 and quantitatively determine which filter provides the requisite noise reduction, as well as the optimal radiation/image quality ratio.

The QA data analysis performed by the program 110 can not only be used prospectively at the time of task presentation, but also retrospectively, to identify the relationship between QA and individual/collective task performance, and make recommendations for improvement. The ability to cross-reference the acquired QA sensor data between multiple sites provides a mechanism for QA meta-analysis. The large sample size through this combined QA analysis by the program 110, creates a statistical power not achievable through a single institutional analysis alone. This provides a mechanism where the program 110 can analyze multiple variables intrinsic to the exam (e.g., clinical indication, patient body habitus), individual stakeholder issues (e.g., radiologist diagnostic accuracy, technologist retake rate) and institutional issues (e.g., mean radiation/image quality ratio, percentage of QA sensor/technologist agreement).

The data analyzed by the program 110 can be divided by the program 110 according to predefined peer groups, so that institutions can be evaluated in comparison with institutions of similar size, patient demographics, or technology being used. In a similar fashion, technologists and/or radiologists can be analyzed by the program 110 relative to their peers with similar clinical experience, educational training, or supporting technology. This QA performance data can in turn be cross-referenced with clinical data by the program 110 (available on the EMR), to determine the relationship between various QA metrics and clinical outcomes (e.g., radiologist diagnostic accuracy, length of stay for hospitalized patients).

Whenever suboptimal QA performance scores are identified by the program 110, notification is electronically sent (with receipt verification) by the program 110 to the involved party, in addition to the multi-disciplinary QA committee at the institution of record. The specific QA scores identified as sub-optimal by the program 110, are sent by the program 110 along with the corresponding peer-review data, identifying the source of the QA deficiency. A series of education/training programs can be created using the program 110 and the QA database 113, the sources for the programs which include a number of sources such as (but which are not limited to) the multi-disciplinary QA teams, professional societies (e.g., American Society of Radiologic Technologists (ASRT), American College of Radiology (ACR), American Association of Physicists in Medicine (AAPM)), and governmental agencies (e.g., Food and Drug Administration (FDA), National Library of Medicine (NLM), Agency for Healthcare Research and Quality (AHRQ), and Nuclear Regulatory Commission (NRC)). Completion of these educational programs by the involved party is recorded in the QA database 113 by the program 110 and used for future tracking of QA performance. Those QA educational programs which demonstrate the highest change in QA performance after completion are prioritized by the program 110 within the QA educational program repository, in the hopes of continuously upgrading QA educational content commensurate with the needs of the user community.

In the event that the QA deficiencies are not improved, additional QA intervention can be instituted by the program 110, including mandating formal mentoring and QA certification programs. At an institutional level, repeated QA deficiencies can result in the program 110 mandating a QA consultation by a pre-certified QA expert in the specific field of interest. Repetitive QA deficiencies or egregious violations of quality/safety could be reported to the appropriate authorities by the program 110, which could trigger suspension of clinical privileges.

The responsibility of QA data analysis and oversight can be designated to a third party non-profit organization with established expertise in the healthcare domain. The validated QA data and peer-review analysis can subsequently be made available for public dissemination through the Internet and print publications, to allow healthcare consumers to make educated decisions as to the quality of service provided.

The QA data and associated analytics could derive a number of interesting outcomes, including new technology development, product testing, and establishment of EBM guidelines.

Another important feature of data derived from the QA sensor 300, 308 is the ability of the program 110 to automatically record, analyze, and report equipment quality control (QC) problems. Certain QA deficiencies (e.g., spatial resolution) are commonly the result of faulty technology (e.g., digital receptor malfunction), and often go unnoticed during routine day-to-day operation, until the QC issue reaches a critical level. Before this critical threshold is realized, many sub-optimal medical images are acquired and interpreted, potentially resulting in misdiagnosis. By incorporating this quantitative and objective data into the program 100 of the QA sensor 300, 308, relatively minor QC deficiencies can be identified by the program 110 and acted upon at an early stage. By the program 110 tracking this data within the institutional QA database 113, ongoing trending analysis can be performed by the program 110, which provides early identification of equipment-related QA deficiencies. In addition, systematic technology-related QA/QC deficiencies can be identified by the program 110 on a large scale basis through meta-analysis of multi-institutional databases. This provides a reliable and reproducible means to identify technology deficiencies (which may be vendor specific) before they would otherwise be detected, and devoid of any subjective bias.

In addition to operator and technology-related etiologies for QA deficiencies, patients can also be the source of QA deficiencies (e.g., motion). By objectifying, identifying, and quantifying these deficiencies using the QA sensor 300, 308, proactive adjustment of acquisition parameters can be performed by the program 110 (i.e., altering number and order of MRI sequences to decrease acquisition time and resultant motion).

As an example, a patient with multiple instances of documented motion errors may be identified a priori (by the program 110 prospective analysis of the QA database 113 prior to exam initiation). The program 110 can identify these QA deficiencies and create a patient-specific QA profile, alerting the technologist of prior QA data points prior to performing the exam. This form of decision support is the direct result of prospective analysis of the QA database 113, which can obviate or reduce future QA deficiencies.

The QA program would operate as follows. The patient would arrive at an imaging department for an examination, and be escorted to an imaging modality for the exam (e.g., a CT).

The patient's identification/authentication would be established using biometrics, as described above. Thereafter, the technologist performing the exam will establish his/her identification/authentication at the modality (i.e., radiographic device 21).

Thereafter, clinical and imaging data will be queried by the program 110 from multiple databases 113 (such as the CPOE, RIS 20, modality 21, PACS 30, EMR) based upon the patient and technologist identifications (see for example, pending U.S. patent application Ser. No. 11/699,348, dated Jan. 30, 2007, U.S. patent application Ser. No. 11/699,349, dated Jan. 30, 2007, U.S. patent application Ser. No. 11/699,350, dated Jan. 30, 2007, U.S. patent application Ser. No. 11/699,344, dated Jan. 30, 2007, U.S. patent application Ser. No. 11/699,351, dated Jan. 30, 2007, and U.S. patent application Ser. No. 11/412,884, dated Apr. 28, 2006, the contents of all of which are herein incorporated by reference in their entirety). The data derived would include: exam type, medical history, pertinent laboratory data, clinical indication for requested exam. The technologist will then manually verify that the exam type, patient and technologist-specific data is correct.

The technologist will then position the QA sensor 300 on the skin surface of the patient over the desired anatomic region for examination (e.g., chest). The QA sensor 300 synchronizes with the QA and other databases 113 of the modality 21 and information systems (CPOE, RIS 20, PACS 30, EMR) via wireless connectivity.

In step 400 (see FIG. 3A), the QA sensor 300 then records pre-acquisition data: Laterality (e.g. right, left), Positioning (e.g. supine, prone), Anatomic region (e.g. thorax), Modality (e.g. CT), Patient identification, Technologist identification, Date and time of exam, Pertinent clinical data (derived from CPOE, RIS 20, PACS 30, EMR), and Default acquisition parameters (derived from patient, exam, and QA databases 113) (i.e., kVp, mAs, CT kernel, collimation, pitch).

The technologist then reviews the QA sensor data as displayed. The program 110 will prompt the technologist to accept or reject the data, and the technologist, in this example, accepts "as is". In an alternate response, the technologist could review the QA sensor data and may make manual edits. Upon acceptance, the technologist verifies the QA sensor data, which is transferred by the program 110, and stored in the QA databases 113 in "verified" format (see step 400, FIG. 3A).

The technologist then returns to the modality 21 console to verify the acquisition parameters, and accepts the acquisition parameters "as is". The technologist may manually edit the acquisition parameters (e.g., ↑ kVp), if desired.

The technologist may then request an electronic consultation of the database 113 for "alternative protocols" based upon new and/or revised clinical/imaging data received from the imaging modality 21 or QA sensor 300 (e.g., undocumented 40 lb. weight gain, outside chest radiograph demonstrated left lung nodule), and entered (automatically or manually) into the databases 113.

The program 110 then can query the QA databases 113 (patient and exam-specific QA databases) for the inputted revised acquisition parameters. Since the QA databases 113 would have records of other studies' acquisition parameters and subjective/objective quality measures, by searching these QA databases 113 for the optimized acquisition parameters, decision support can be provided to the technologist to assist with determining the optimum acquisition parameters, along with the QA sensor 300 data measurements acquired. The program 110 can then provide the technologist with revised acquisition default parameters in step 401 (see FIG. 3A), and the technologist may accept the revised parameters "as is", or again manually edit any computer-derived acquisition parameters.

Once the acquisition parameters have been established, the technologist may begin the exam acquisition. At this point, technologist has two options: 1) to obtain a "pre-scan" QA test image, or 2) to proceed with the "final" exam acquisition.

In the first option, the program 110 derived acquisition parameters are adjusted by the program 110 or manually, for an ultra-low dose test QA image ($1/10^{th}$ standard image dose). The technologist then may acquire the QA test image using the radiographic device 21, and the data is received and stored in step 400. The options available for taking of the QA test image include: 1) optimization of the acquisition parameters; 2) assessment of the anatomic positioning; and 3) radiation dose optimization. It should be noted that these options are not mutually exclusive and any combination or all of these options can be performed using the QA Test Image In the optimization of the acquisition parameters, the QA sensor 300 derives the individual QA metrics from the test image taken in step 402, the parameters including a) Motion; b) Spatial resolution c) Contrast resolution; d) Radiation dose; and e) Noise. Once the data is optimized, the technologist can accept the program 110 derived acquisition parameters from the QA Test Image, and may and proceed to "final" image acquisition. Alternatively, the technologist can manually edit the program 110 derived acquisition parameters and the proceed to acquire the "final" image.

As described above, in step 402, the assessment of Anatomic Positioning includes a visual display of the test image, of the anatomic field of view (FOV) at the imaging modality 21 console. Once the test image is displayed, further analysis of the anatomic positioning can be done by the program 110, or manually by technologist. Thereafter, the program 110 can analyze the test QA image for positioning (utilizing key anatomic landmarks for inclusion in the FOV) in step 403. Then, the program 110 can provide automated positioning feedback to the technologist based on an analysis of key anatomic landmarks. Thus, the technologist may accept the anatomic positioning "as is", or may manually adjust the FOV in accordance with positioning feedback from the program 110 in step 404. This positioning determination can be presented by the program 110 as a pass/fail scenario, where the technologist can accept (pass) or reject (fail) the data provided (see step 405). The technologist then may manually review the FOV to ensure required anatomic landmarks are contained within the image, and either accept the FOV "as is", or may manually modify the FOV to optimize positioning deficiencies.

With respect to the radiation dose optimization, the technologist may obtain an ultra-low dose QA Test image, and the image may be correlated with a quantitative measurement tool of image quality (e.g., JND-metric or PSNR), as in step 403. Thereafter, the program 110 may quantitatively define the amount of noise within the imaging dataset pixels, and define an image quality threshold to be maintained (e.g., 1 JND).

The program 110 may then query the Radiation Scorecard and QA databases 113 in step 403, to determine, for example, optimum exposure parameters based on exam type, technology used, patient profile, and image quality threshold requirements. The program 110 will then utilize decision support tools (e.g., post-acquisition image processing and CAD algorithm) selected based on the specific exposure parameters to determine recommendations for the technologist, as in step 404, and to determine best practice guidelines.

If the technologist decides to proceed with the "final" exam acquisition, he/she can perform the exam acquisition using verified acquisition parameters as described above with respect to steps 400-401. Thereafter, the QA sensor 300 provides automatic measurements of individual and collective QA metrics (using individual phantoms and measuring devices contained within the QA sensor 300), such as: a) Motion; b) Spatial resolution; c) Contrast resolution; d) Noise; and e) Radiation dose, as in step 402. In particular, the Radiation dose can be measured by: 1) skin entrance dose (directly measured by QA sensor 300 on ventral patient skin surface); or 2) a specific organ dose (calculated by (two) QA sensors 300 placed on ventral and dorsal patient skin surfaces).

In step 403, the QA sensor 300 quantitative measurements are correlated by the program 110 with incremental QA grading scales, and tied to individual and collective QA measurements (i.e., cross-referenced with institutional databases 113).

In step 404, the program 100 will determine recommendations for quality assurance, using a representative grading scale tied to optimization of individual QA metrics. For example, scores may be identified as:

1—Poor QA score (>2 standard deviations (SD) below the mean*).

* The mean values would be derived from the QA databases 113, specific to the exam type and patient profile).

2—Below Average QA Score (1-2 SD below mean)
3—Average QA Score (±1 SD of mean)
4—Above Average QA Score (1-2 SD above mean)
5—Excellent QA Score (>2 SD above mean)

Thus, the program 110 can generate a quality assurance score, where the representative grading scale is tied to the overall (comprehensive) exam quality (i.e., mathematical rule sets would be derived for determining overall (comprehensive) exam pass/fail grades).

A—High Pass
B—Pass
C—Low Pass
D—Fail

The criteria and weighting of individual QA metrics for determining pass/fail gradations can be modified by the program 110 according to specific end-user requirements and preferences. Thus, the program 110 will identify the exam as a "pass" or "fail" according to step 405.

In an exam QA Pass, the examination is accepted by the technologist "as is", and the accepted imaging dataset is transferred by the program 110 to the PACS 30 for interpretation in step 406. In this step, the individual and collective QA metrics data are transferred by the program 110 to the QA databases 113 in "final" formats, and the updated QA databases 113 will contain newly acquired QA data which are included in any future QA analyses.

In the event of an exam Marginal QA Pass, the program 110 will analyze the QA database 113 and the individual QA metrics in step 406, and present options to the user for re-acquisition (along with additional radiation exposure estimates). Thus, the technologist may be presented with three (3) options: 1) accept exam "as is" without image processing; 2) accept the exam "as is" with additional program 110 derived (post-acquisition) image processing to enhance identified QA deficiencies; or 3) retake the exam (in entirety or in part). In this third option, the technologist will then follow the pathway of an "Exam QA Fail" as described below. Thus, once the exam has been accepted "as is", the pathway for "Exam QA Pass" will be followed and the imaging dataset is transferred to the PACS 30 as in step 406.

In the event of an exam QA Fail, the individual acquisition parameters will be modified by the program 110 (using QA database 113), based on the analysis of the sub-optimal QA metrics (e.g., poor contrast resolution) as in step 407. The technologist will then be provided with three (3) options for proceeding: 1) accept the program 110 derived modification of acquisition parameters and reacquire the imaging study (in part or entirety) as in step 408; 2) manually adjust the acquisition parameters; or 3) abort the exam due to "uncorrectable" QA deficiencies, which can be due to equipment failure (e.g., faulty detector) as in step 409, or patient failure (e.g., excessive motion due to non-compliance). If, for example, the QA sensor 300 is not operating correctly, recalibration may be required as in step 412. If the examination is aborted, mandatory radiologist and/or clinician consultation is required, as in steps 407-408 and in step 418 (see FIG. 3B).

Thus, the outcomes and analysis of the program 110 derived QA data will include: 1) an automated decision to "pass" or "fail" the acquired image (step 405); 2) recommendations for refined image acquisition parameters (on failed images) (step 408); 3) the identification of QA deficiencies caused by technology failure (QC) (steps 409 and 412); 4) the identification of QA deficiencies caused by operator error (step 407-408 and 418); 5) the identification of patient-related QA deficiencies (step 404, and 407-408); 6) the automated application by the program 110 of post-acquisition image processing (step 406); and 7) recommendations for radiation dose optimization (steps 401, or 402-403).

In step 410, in the event of issues as described above, clinician input and the statistical analysis of data inputs are provided received by the program 110, for inclusion in the exam interpretation. Thereafter, as described above, a comprehensive QA score can be provided in step 411.

If this comprehensive score is accepted, as in step 413, then the score can be provided, along with others, for third party review by institutional bodies, as described above, and potentially for public dissemination in step 414.

If the QA score is not accepted, then in one option, additional analysis can be performed on the data in step 415, and further review taken by supervisors in step 416, as described previously. In another option, the non-accepted QA score can be provided for trending analysis in step 419, or for third party review in step 414.

If further review determines that additional training is required of the operator, then an alert can be forwarded to the appropriate parties, and the corrective measures, retaken measurements (from step 408), or databases 113 and QA scores may be reviewed by a radiologist or clinician in step 418, as described previously. In addition, trending analysis is performed on this information in step 419, in order to determine if QC deficiencies are taking places, as in step 409, and to determine best practice guidelines, as described previously.

Further, based on steps 417-419, training can be recommended by the program 110, or mentoring and or additional QA certification, as in step 420, in order to improve the QA of the data, as described above.

Thus, an optimum quality program for the taking of medical images that would provide standards for QA and QC in an identical and reproducible manner, regardless of the specific technology and personnel acquiring the imaging data, may be achieved. The QA sensor 300 of the present invention, can quantify the QA process, and these metrics are then automatically recorded and used to track and analyze individual and collective QA performance and patient safety measures.

Thus, it should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A sensor using in a medical imaging examination comprising:
   a sensor body having an upper surface and a flat lower surface, said flat lower surface being divided into more than one portioned segment;
   a plurality of sensors and test patterns embedded into said flat lower surface, within each said portioned segments;
   wherein each of said sensors and test patterns in each said portioned segment, take predetermined quality assurance metrics, said quality assurance metrics including more than least-one of motion, contrast resolution, spatial resolution, radiation dose, noise, and anatomic positioning, to optimize image acquisition during the medical imaging examination.

2. The sensor according to claim 1, further comprising a hole disposed within at least one said portioned segment, such that motion in acquiring data by said sensors and test patterns can be detected by a measurement of an outline of said hole.

3. The sensor according to claim 1, further comprising:
   a wireless module which forwards said quality assurance metrics to an external database.

4. The sensor according to claim 1, further comprising:
   a memory for saving data obtained on said quality assurance metrics.

5. A method of providing a quality assurance program for a medical imaging examination, comprising:
   measuring quality assurance metrics, including more than one of motion, contrast resolution, spatial resolution, radiation-goes dose, noise, and anatomic positioning, using a quality assurance sensor, during the medical imaging examination;
   wherein said quality assurance sensor includes a flat lower surface being divided into more than one portioned segment, with a plurality of sensors and test patterns embedded into said flat lower surface, within each said portioned segments, such that each of said sensors and test patterns measure said quality assurance metrics;
   performing an analysis of data from said quality assurance metrics from said more than one portioned segment, and comparing said data with norms for said quality assurance metrics data stored in said database; and
   providing quality assurance recommendations in real-time for adjustment of said quality assurance metrics during the medical imaging examination.

6. The method according to claim 5, further comprising:
   providing pass/fail recommendations based upon predetermined image quality standards for said quality assurance metrics data.

7. The method according to claim 5, further comprising:
   analyzing said quality assurance metrics data and providing recommendations for improvements in image quality.

8. The method according to claim 7, further comprising:
   providing recommendations to optimize post-acquisition image processing.

9. The method according to claim 5, further comprising:
   cross-referencing said quality assurance metrics data with institutional quality assurance databases to establish best practice guidelines.

10. The method according to claim 6, further comprising:
    receiving input from a radiologist or clinician regarding said quality assurance metrics data and said image quality.

11. The method according to claim 10, further comprising:
    interpreting said input and said quality assurance metrics data; and
    generating a quality assurance score based on said input and said quality assurance metrics data for said imaging quality of the medical imaging examination.

12. The method according to claim 11, further comprising:
    incorporating individual quality assurance scores into a comprehensive quality assurance score which selectively weights individual quality assurance metrics data to overall image quality.

13. The method according to claim 11, further comprising:
    performing additional analysis of said quality assurance metrics data when said quality assurance score is not acceptable.

14. The method according to claim 13, further comprising:
reviewing and analyzing actions taken by a technologist during the medical imaging examination; and
recommending further training for said technologist when said actions do not meet internal standards.

15. The method according to claim 7, further comprising:
determining quality control deficiencies in the medical imaging examination; and
correcting said deficiencies.

16. The method according to claim 15, wherein said deficiencies require recalibration of said quality assurance sensor.

17. The method according to claim 5, further comprising:
generating an alert when said analysis and said comparison determines there is a discrepancy in said quality assurance metrics data; and
obtaining images from at least one quality assurance database to assist in classification of said discrepancy.

18. The method according to claim 5, further comprising:
generating an alert when said quality assurance metrics analysis shows a quality assurance deficiency; and
recommending correcting measures to correct said deficiency, including retaking of the medical imaging examination after said corrective measures are taken.

19. The method according to claim 5, wherein default image acquisition parameters are provided prior to the medical imaging examination, with recommended exposure parameters and protocols based upon stored quality assurance metrics data.

20. The method according to claim 11, further comprising:
forwarding said quality assurance metrics data and said quality assurance scores to third party reviewers including peer groups, and professional institutional bodies.

21. The method according to claim 11, further comprising:
cross-referencing said quality assurance metrics data and said quality assurance scores with stored clinical data to determine a relationship between said quality assurance metrics data and quality assurance scores and clinical outcomes.

22. The method according to claim 14, further comprising:
generating an alert whenever suboptimal quality assurance scores are identified, for review of said scores by involved third parties.

23. The method according to claim 22, further comprising:
creating educational or training programs to correct any deficiencies in quality assurance, and/or requiring mentoring or quality assurance certification programs to correct same.

24. The method according to claim 14, further comprising:
performing trending analysis of said actions, said quality assurance metrics data and said quality assurance scores.

25. The method according to claim 21, further comprising:
performing trending analysis of said relationship between said quality assurance metrics data and quality assurance scores, and clinical outcomes.

26. Non-transitory computer-readable medium containing executable instructions on providing a quality assurance program for a medical imaging examination, comprising:
measuring quality assurance metrics, including more than one of motion, contrast resolution, spatial resolution, radiation dose, noise, and anatomic positioning, using a quality assurance sensor, during the medical imaging examination;
wherein said quality assurance sensor includes a flat lower surface being divided into more than one portioned segment, with a plurality of sensors and test patterns embedded into said flat lower surface, within each said portioned segments, such that each of said sensors and test patterns measure said quality assurance metrics;
performing an analysis of data from said quality assurance metrics from said more than one portioned segment, and comparing said data with norms for said quality assurance metrics data stored in said database; and
providing quality assurance recommendations in real-time for adjustment of said quality assurance metrics during the medical imaging examination.

27. A computer system which provides a quality assurance program for a medical imaging examination, comprising:
at least one memory containing at least one program comprising the steps of:
measuring quality assurance metrics, including more than one of motion, contrast resolution, spatial resolution, radiation dose, noise, and anatomic positioning, using a quality assurance sensor, during the medical imaging examination;
wherein said quality assurance sensor includes a flat lower surface being divided into more than one portioned segment, with a plurality of sensors and test patterns embedded into said flat lower surface, within each said portioned segments, such that each of said sensors and test patterns measure said quality assurance metrics;
performing an analysis of data from said quality assurance metrics from said more than one portioned segment, and comparing said data with norms for said quality assurance metrics data stored in said database; and
providing quality assurance recommendations in real-time for adjustment of said quality assurance metrics during the medical imaging examination; and
at least one processor which executes said program.

* * * * *